(12) United States Patent
Braga

(10) Patent No.: US 9,168,355 B2
(45) Date of Patent: Oct. 27, 2015

(54) ACUTE HEMODIALYSIS CATHETER ASSEMBLY

(75) Inventor: Richard Braga, Taunton, MA (US)

(73) Assignee: Covidien LP, Mansfield, MA (US)

( * ) Notice: Subject to any disclaimer, the term of this patent is extended or adjusted under 35 U.S.C. 154(b) by 2359 days.

(21) Appl. No.: 11/541,043

(22) Filed: Sep. 29, 2006

(65) Prior Publication Data

US 2008/0082080 A1  Apr. 3, 2008

(51) Int. Cl.
  *A61M 3/00* (2006.01)
  *A61M 25/00* (2006.01)
  *A61M 1/36* (2006.01)

(52) U.S. Cl.
  CPC ........... *A61M 25/007* (2013.01); *A61M 1/3661* (2014.02); *A61M 25/0069* (2013.01); *A61M 25/0029* (2013.01); *A61M 25/0032* (2013.01); *A61M 2025/0031* (2013.01)

(58) Field of Classification Search
  CPC ................... A61M 1/3661; A61M 2025/0031; A61M 25/003; A61M 25/0032; A61M 25/0068
  USPC ............. 604/6.16, 29, 93.01, 102.01–102.03, 604/118–121, 264, 523, 43
  See application file for complete search history.

(56) References Cited

U.S. PATENT DOCUMENTS

| | | | |
|---|---|---|---|
| 4,403,983 A | 9/1983 | Edelman et al. | |
| 4,493,696 A | 1/1985 | Uldall | |
| 4,568,329 A | 2/1986 | Mahurkar | |
| 4,583,968 A | 4/1986 | Mahurkar | |
| 4,619,643 A | 10/1986 | Bai | |
| 4,626,240 A | 12/1986 | Edelman et al. | |
| 4,643,711 A | 2/1987 | Bates | |
| 4,692,141 A | 9/1987 | Mahurkar | |
| 4,769,005 A | 9/1988 | Ginsburg et al. | |
| 4,772,268 A | 9/1988 | Bates | |
| 4,772,269 A | 9/1988 | Twardowski et al. | |
| 4,795,439 A | 1/1989 | Guest | |
| 4,808,155 A | 2/1989 | Mahurkar | |
| 4,808,156 A | 2/1989 | Dean | |
| 4,842,582 A * | 6/1989 | Mahurkar | 604/43 |
| 4,895,561 A * | 1/1990 | Mahurkar | 604/43 |

(Continued)

FOREIGN PATENT DOCUMENTS

EP  0 299 622  1/1989
EP  0 554 722 A1  8/1993

(Continued)

OTHER PUBLICATIONS

European Search Report, Application No. EP 07 25 3689 dated Apr. 17, 2008.

*Primary Examiner* — Phillip Gray
(74) *Attorney, Agent, or Firm* — John Paul Mello, Esq.

(57) ABSTRACT

A medical catheter includes an elongate catheter member defining a longitudinal axis, and a transverse axis transverse to the longitudinal axis, and having a proximal end and a distal end. The elongate catheter member includes an outer member and at least one longitudinal lumen within the outer member for passage of fluids. The outer member has an elongate opening therethrough in communication with the at least one longitudinal lumen and being spaced from the distal end and bound by wall portions of the outer member. The elongate opening permits fluids to pass between the at least one longitudinal lumen and locations external to the elongate catheter member, and defines a transverse dimension increasing from proximal to distal.

20 Claims, 7 Drawing Sheets

(56) References Cited

U.S. PATENT DOCUMENTS

| | | | |
|---|---|---|---|
| 4,897,079 A | 1/1990 | Zaleski et al. | |
| 4,961,809 A | 10/1990 | Martin | |
| 4,995,865 A | 2/1991 | Gahara et al. | |
| 5,009,636 A | 4/1991 | Wortley et al. | |
| 5,035,399 A | 7/1991 | Rantanen-Lee | |
| 5,041,083 A | 8/1991 | Tsuchida et al. | |
| 5,053,004 A | 10/1991 | Markel et al. | |
| 5,053,023 A | 10/1991 | Martin | |
| 5,057,073 A | 10/1991 | Martin | |
| 5,059,170 A | 10/1991 | Cameron | |
| 5,085,632 A | 2/1992 | Ikada et al. | |
| 5,106,368 A | 4/1992 | Uldall et al. | |
| 5,135,599 A | 8/1992 | Martin et al. | |
| 5,156,592 A | 10/1992 | Martin et al. | |
| 5,167,623 A * | 12/1992 | Cianci et al. | 604/43 |
| 5,188,593 A | 2/1993 | Martin | |
| 5,190,520 A | 3/1993 | Fenton, Jr. et al. | |
| 5,195,962 A | 3/1993 | Martin et al. | |
| 5,197,951 A | 3/1993 | Mahurkar | |
| 5,209,723 A | 5/1993 | Twardowski et al. | |
| 5,219,335 A | 6/1993 | Willard et al. | |
| 5,221,255 A | 6/1993 | Mahurkar et al. | |
| 5,221,256 A * | 6/1993 | Mahurkar | 604/43 |
| 5,308,338 A | 5/1994 | Helfrich | |
| 5,346,471 A | 9/1994 | Raulerson | |
| 5,348,536 A | 9/1994 | Young et al. | |
| 5,360,397 A | 11/1994 | Pinchuk | |
| 5,364,344 A | 11/1994 | Beattie et al. | |
| 5,374,245 A | 12/1994 | Mahurkar | |
| 5,378,230 A | 1/1995 | Mahurkar | |
| 5,380,276 A | 1/1995 | Miller et al. | |
| 5,395,316 A | 3/1995 | Martin | |
| 5,403,291 A | 4/1995 | Abrahamson | |
| 5,405,341 A | 4/1995 | Martin | |
| 5,451,206 A | 9/1995 | Young | |
| 5,464,398 A | 11/1995 | Haindl | |
| 5,472,417 A | 12/1995 | Martin et al. | |
| 5,480,380 A | 1/1996 | Martin | |
| 5,486,159 A | 1/1996 | Mahurkar | |
| 5,489,278 A | 2/1996 | Abrahamson | |
| 5,509,897 A | 4/1996 | Twardowski et al. | |
| 5,556,390 A | 9/1996 | Hicks | |
| 5,569,182 A | 10/1996 | Twardowski et al. | |
| 5,571,093 A | 11/1996 | Cruz et al. | |
| D381,420 S | 7/1997 | Musgrave et al. | |
| D384,411 S | 9/1997 | Musgrave et al. | |
| D384,741 S | 10/1997 | Musgrave et al. | |
| 5,683,640 A | 11/1997 | Miller et al. | |
| 5,685,867 A | 11/1997 | Twardowski et al. | |
| 5,702,365 A | 12/1997 | King | |
| 5,718,678 A | 2/1998 | Fleming, III | |
| 5,776,096 A * | 7/1998 | Fields | 604/43 |
| 5,797,869 A | 8/1998 | Martin et al. | |
| 5,807,311 A | 9/1998 | Palestrant | |
| 5,807,329 A | 9/1998 | Gelman | |
| 5,810,789 A | 9/1998 | Powers et al. | |
| 5,830,184 A | 11/1998 | Basta | |
| 5,830,196 A | 11/1998 | Hicks | |
| 5,868,717 A | 2/1999 | Prosl | |
| 5,947,953 A | 9/1999 | Ash et al. | |
| 5,961,485 A | 10/1999 | Martin | |
| 5,961,486 A | 10/1999 | Twardowski et al. | |
| 5,976,103 A | 11/1999 | Martin | |
| 5,989,206 A | 11/1999 | Prosl et al. | |
| 5,989,213 A | 11/1999 | Maginot | |
| 5,993,437 A | 11/1999 | Raoz | |
| 6,001,079 A | 12/1999 | Pourchez | |
| 6,004,310 A | 12/1999 | Bardsley et al. | |
| 6,099,519 A | 8/2000 | Olsen et al. | |
| 6,123,725 A | 9/2000 | Aboul-Hosn | |
| 6,126,631 A | 10/2000 | Loggie | |
| 6,146,354 A | 11/2000 | Beil | |
| 6,156,016 A | 12/2000 | Maginot | |
| 6,190,349 B1 | 2/2001 | Ash et al. | |
| 6,190,371 B1 | 2/2001 | Maginot et al. | |
| 6,206,849 B1 | 3/2001 | Martin et al. | |
| 6,273,875 B1 | 8/2001 | Siman et al. | |
| 6,280,423 B1 | 8/2001 | Davey et al. | |
| 6,293,927 B1 | 9/2001 | McGuckin, Jr. | |
| 6,342,120 B1 | 1/2002 | Basta | |
| 6,346,090 B1 | 2/2002 | Liska et al. | |
| 6,394,141 B2 | 5/2002 | Wages et al. | |
| 6,409,700 B1 | 6/2002 | Siegel, Jr. et al. | |
| 6,447,488 B2 | 9/2002 | Estabrook et al. | |
| 6,461,321 B1 | 10/2002 | Quinn | |
| 6,475,207 B1 | 11/2002 | Maginot et al. | |
| 6,482,169 B1 | 11/2002 | Kuhle | |
| 6,506,182 B2 | 1/2003 | Estabrook et al. | |
| 6,579,261 B1 | 6/2003 | Kawamura | |
| 6,585,705 B1 | 7/2003 | Maginot et al. | |
| 6,592,542 B2 | 7/2003 | Childers et al. | |
| 6,592,558 B2 | 7/2003 | Quah | |
| 6,595,966 B2 | 7/2003 | Davey et al. | |
| 6,620,118 B1 | 9/2003 | Prosl et al. | |
| 6,638,242 B2 | 10/2003 | Wilson et al. | |
| 6,692,473 B2 | 2/2004 | St. Cyr et al. | |
| 6,695,832 B2 | 2/2004 | Schon et al. | |
| 6,719,749 B1 | 4/2004 | Schweikert et al. | |
| 6,723,084 B1 | 4/2004 | Maginot et al. | |
| 6,730,096 B2 | 5/2004 | Basta | |
| 6,743,218 B2 | 6/2004 | Maginot et al. | |
| 6,749,580 B2 | 6/2004 | Gloukhoff et al. | |
| 6,758,836 B2 | 7/2004 | Zawacki | |
| 6,786,884 B1 | 9/2004 | DeCant, Jr. et al. | |
| 6,808,510 B1 | 10/2004 | DiFiore | |
| 6,814,718 B2 * | 11/2004 | McGuckin et al. | 604/264 |
| 6,858,019 B2 | 2/2005 | McGuckin, Jr. et al. | |
| 6,872,198 B1 | 3/2005 | Wilson et al. | |
| 6,911,014 B2 | 6/2005 | Wentling et al. | |
| 6,921,396 B1 | 7/2005 | Wilson et al. | |
| 6,942,635 B2 | 9/2005 | Rosenblatt et al. | |
| 6,942,653 B2 | 9/2005 | Quinn | |
| 6,966,886 B2 | 11/2005 | Appling | |
| 6,969,381 B2 | 11/2005 | Voorhees | |
| 6,976,973 B1 | 12/2005 | Ruddell et al. | |
| 6,986,752 B2 | 1/2006 | McGuckin, Jr. et al. | |
| 6,991,625 B1 | 1/2006 | Gately et al. | |
| 7,008,395 B1 | 3/2006 | Loggie | |
| 7,008,412 B2 | 3/2006 | Maginot | |
| 7,011,645 B2 | 3/2006 | McGuckin, Jr. et al. | |
| 7,013,928 B2 | 3/2006 | Navis | |
| 7,048,680 B2 | 5/2006 | Viole et al. | |
| 7,066,914 B2 | 6/2006 | Andersen | |
| 7,077,829 B2 | 7/2006 | McGuckin, Jr. et al. | |
| 7,141,035 B2 * | 11/2006 | Haggstrom | 604/43 |
| 7,569,029 B2 * | 8/2009 | Clark | 604/43 |
| 2002/0121282 A1 | 9/2002 | McGuckin | |
| 2003/0032918 A1 * | 2/2003 | Quinn | 604/43 |
| 2003/0093029 A1 | 5/2003 | McGuckin, Jr. | |
| 2003/0191425 A1 | 10/2003 | Rosenblatt | |
| 2004/0167463 A1 * | 8/2004 | Zawacki et al. | 604/43 |
| 2004/0249337 A1 | 12/2004 | DiFiore | |
| 2005/0033222 A1 * | 2/2005 | Haggstrom et al. | 604/43 |
| 2005/0085765 A1 | 4/2005 | Voorhees | |
| 2005/0090776 A1 | 4/2005 | McGuckin, Jr. et al. | |
| 2005/0215978 A1 | 9/2005 | Ash | |
| 2005/0228339 A1 | 10/2005 | Clark | |
| 2005/0267400 A1 | 12/2005 | Haarala et al. | |
| 2005/0288623 A1 | 12/2005 | Hjalmarsson | |
| 2006/0004325 A1 | 1/2006 | Hamatake et al. | |
| 2007/0100298 A1 | 5/2007 | Appling | |

FOREIGN PATENT DOCUMENTS

| | | |
|---|---|---|
| EP | 0 322 225 B1 | 2/1995 |
| EP | 0 713 406 B1 | 3/1998 |
| EP | 0 570 530 B1 | 8/1999 |
| EP | 0 555 780 B1 | 9/1999 |
| EP | 1 144 039 B1 | 12/2005 |
| WO | WO 95/04567 A1 | 2/1995 |
| WO | WO 97/37699 A1 | 10/1997 |
| WO | WO 98/41277 | 9/1998 |
| WO | WO 99/38550 | 8/1999 |
| WO | WO 99/65557 | 12/1999 |

(56) References Cited

FOREIGN PATENT DOCUMENTS

| WO | WO 01/91845 A1 | 12/2001 |
| WO | WO 02/13899 A1 | 2/2002 |
| WO | WO 02/18004 A3 | 3/2002 |
| WO | WO 03/033049 A3 | 4/2003 |
| WO | WO 03/066148 A1 | 8/2003 |
| WO | WO 2004/093956 A1 | 11/2004 |
| WO | WO 2005/023336 A2 | 3/2005 |
| WO | WO 2005/077449 A1 | 8/2005 |
| WO | WO 2005/084741 A1 | 9/2005 |
| WO | WO 2006/014339 A2 | 2/2006 |

* cited by examiner

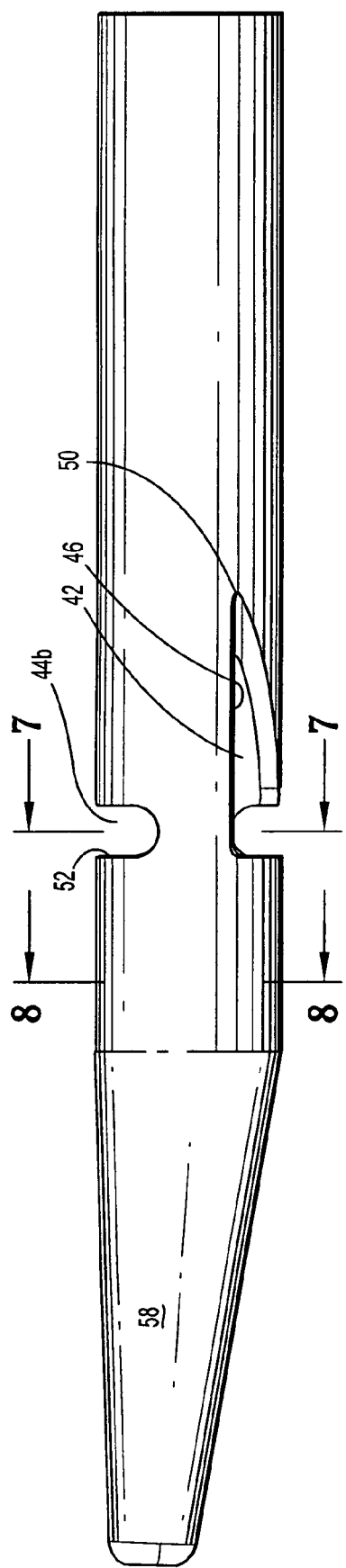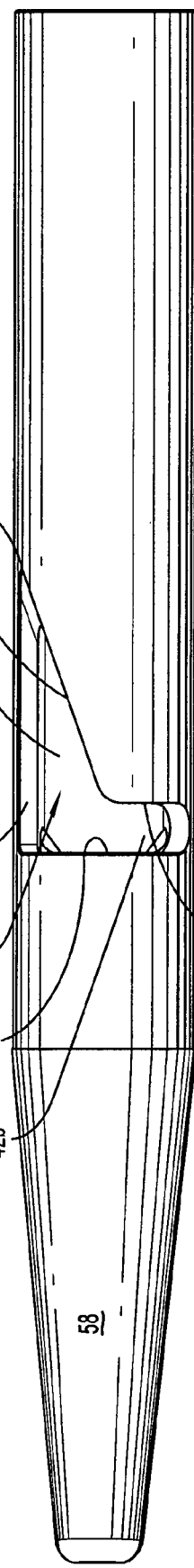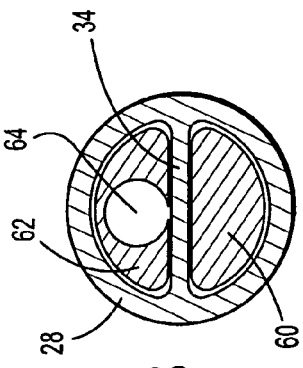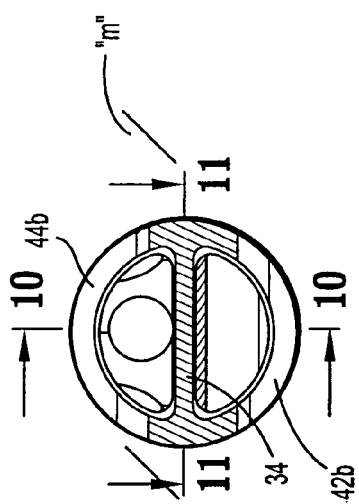

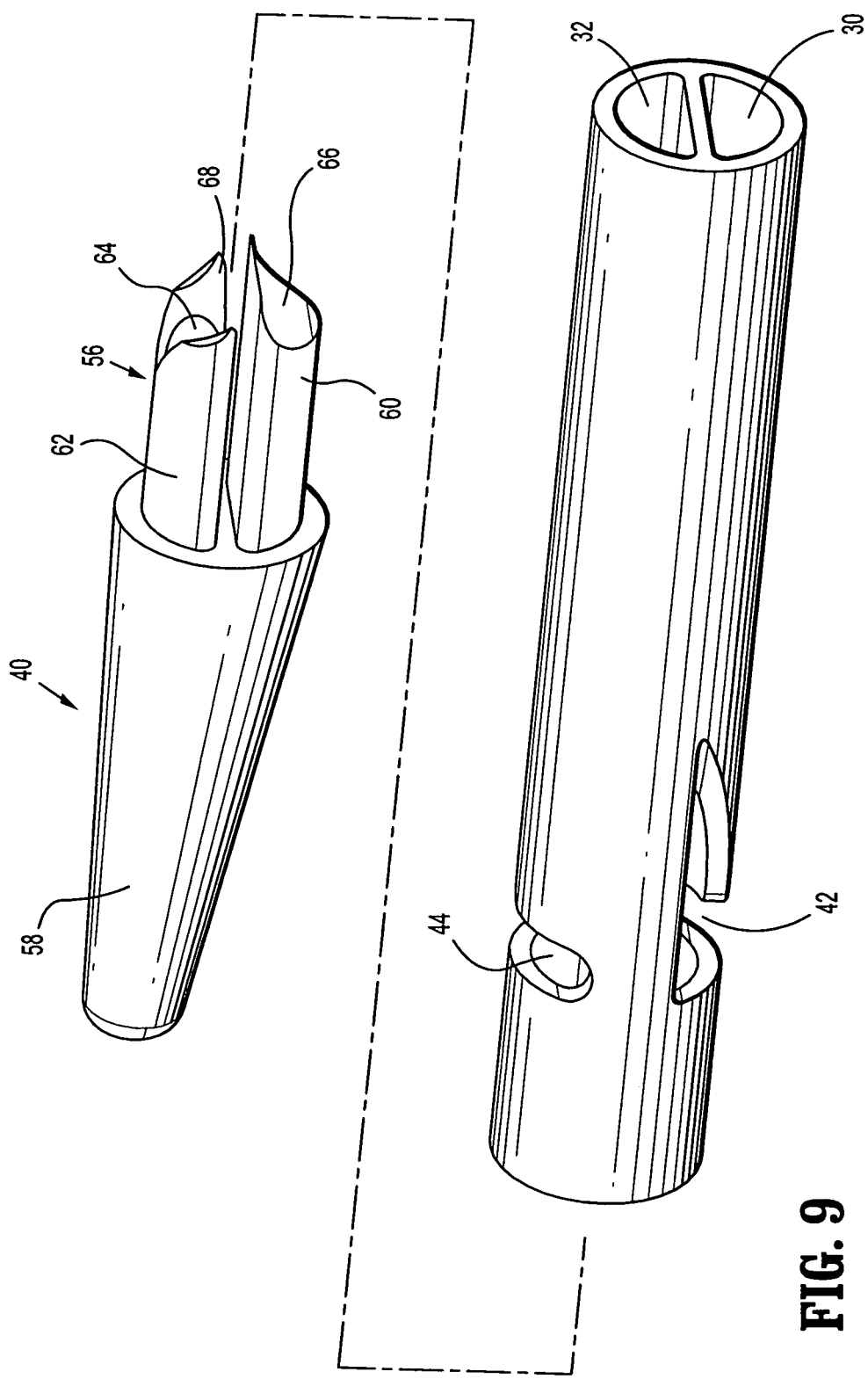

ACUTE HEMODIALYSIS CATHETER ASSEMBLY

BACKGROUND

1. Technical Field

The present disclosure relates to a catheter assembly, and, in particular, relates to a hemodialysis catheter adapted to facilitate bidirectional fluid flow.

2. Description of the Related Art

Catheters are flexible medical instruments intended for the withdrawal and introduction of fluids relative to body cavities, ducts and vessels. Catheters have particular application in hemodialysis procedures where blood is withdrawn from a blood vessel for treatment and subsequently returned to the blood vessel for circulation. Known hemodialysis catheters include multiple lumens, such as dual lumen or triple lumen catheters, permitting bi-directional fluid flow within the catheter whereby one lumen is dedicated for withdrawal of blood and the other lumen is dedicated for returning the treated blood to the vessel. During an exemplary hemodialysis procedure, a multiple lumen catheter is inserted into a body and blood is withdrawn through an arterial lumen of the catheter. The removed blood is directed to a hemodialysis unit which dialyzes, or purifies, the blood to remove waste and toxins. The dialyzed blood is returned to the patient through a venous lumen of the catheter.

Conventional hemodialysis catheters incorporate various catheter tip designs, such as a staggered arterial (inlet) and venous (outlet) design, to ensure blood returning to the patient will be expelled downstream from the arterial inlet which is located upstream to draw the blood from the subject. Unfortunately, poor flow performance is a common problem with hemodialysis catheters, typically, due to occlusion resulting from fibrin sheath formation, thrombus formation and positional occlusion. Flow occlusion is primarily caused by blockage of the arterial lumen. Resolving poor flow is required to deliver the dialysis treatment to the patient. Current measures taken to resolve flow occlusion include repositioning the patient, flushing the lumens and reversing the blood lines of the catheter to the hemodialysis unit. This, however, creates a situation where cleaned blood is expelled upstream relative to the catheter inlet, which undesirably increases the potential for clean blood to be drawn back into the catheter resulting in "recirculation" of the blood. "Recirculation" creates inefficient dialysis by increasing treatment time to reach prescribed blood cleanliness levels.

SUMMARY

Accordingly, the present disclosure is directed to further improvements in hemodialysis catheters and systems used therewith. A medical catheter includes an elongate catheter member defining a longitudinal axis and a transverse axis, and having a proximal end and a distal end. The elongate catheter member includes an outer member and at least one longitudinal lumen within the outer member for passage of fluids. The outer member has an elongate opening therethrough in communication with the at least one longitudinal lumen and being spaced from the distal end and bound by wall portions of the outer member. The elongate opening permits fluids to pass between the at least one longitudinal lumen and locations external to the elongate catheter member, and defines a transverse dimension increasing from proximal to distal.

The wall portions of the outer member may include first and second sides extending at least along the longitudinal axis. At least one of the first and second sides is arranged to diverge outwardly with relation to the longitudinal axis from proximal to distal to thereby increase the transverse dimension of the elongate opening. The first and second sides may be arranged to generally intersect at a proximal location and extend along the longitudinal axis. The wall portions of the outer member further may include an end wall extending at least along the transverse axis. The transverse dimension of the elongate opening may be greatest adjacent the end wall.

In another alternative, the wall portions include an intermediate wall coterminous with the first side and extending outwardly therefrom. The intermediate wall is arranged in general parallel relation with the end wall. The intermediate wall and the end wall generally may extend along the transverse axis in general transverse relation to the longitudinal axis.

The elongate catheter may include first and second longitudinal lumens and corresponding first and second elongate openings within the outer member in communication with the first and second longitudinal lumens and being bound by respective wall portions of the outer member. The first and second elongate openings are arranged in symmetrical relation with respect to a median plane bisecting the elongate catheter member.

In another embodiment, a medical catheter includes an elongate catheter member defining a longitudinal axis, and having a proximal end and a distal end. The elongate catheter member includes an outer member and at least one longitudinal lumen within the outer member. The outer member has an elongate opening therethrough in fluid communication with the at least one longitudinal lumen and being at least bound by inner opening surfaces of the outer member. The elongate opening defines an effective area along the longitudinal axis which increases from proximal to distal, whereby when in a first mode of operation of the elongated catheter member, fluids are substantially withdrawn through a proximal segment of the elongate opening and into the at least one longitudinal lumen, and when in a second mode of operation of the elongated catheter member fluids are delivered from the at least one longitudinal lumen and substantially through a distal segment of the elongate opening. The inner opening surfaces of the outer member include first and second side opening surfaces which generally converge at a proximal location. The elongate opening may define a general tear drop shaped portion. Preferably, the proximal segment of the elongate opening includes the tear drop shaped portion and the distal segment of the elongate opening includes a general polygonal-shaped portion.

The elongate catheter may include first and second longitudinal lumens and corresponding first and second elongate openings within the outer member in communication with the first and second longitudinal lumens. The first and second elongate openings are arranged in symmetrical relation with respect to a median plane bisecting the elongate catheter member. As a further alternative, the elongate catheter includes first, second and third longitudinal lumens and corresponding first, second and third elongate openings within the outer member in communication with the first, second and third longitudinal lumens.

In another embodiment, a dialysis catheter includes an elongate catheter member having an outer member defining proximal and distal ends and a longitudinal axis, and having first and second longitudinal lumens arranged in side by side relation. The outer member includes first and second openings defined within wall surfaces of the outer member and arranged in symmetrical relation with respect to a longitudinal bisecting plane bisecting the elongate catheter member.

The first and second openings are in respective fluid communication with the first and second longitudinal lumens and each defines an area within the wall surfaces greater at a distal location of the elongate opening relative to a proximal location of the elongate opening. The first and second longitudinal lumens are each selectively adapted for removal or delivery of fluids where the fluids may be substantially withdrawn through the area adjacent the proximal location of the opening and where the fluids may be delivered through the area adjacent the distal location of the elongate opening.

A catheter tip member may be mounted to the catheter member. The catheter tip member may define a tapered configuration. The catheter tip member further may include a guide wire lumen therethrough. In one embodiment, the catheter tip member includes first and second mounting extensions which are receivable within the respective first and second longitudinal lumens of the catheter member to connect the catheter tip member to the catheter member. The mounting extensions may include internal contoured wall surfaces which cooperate to direct and receive fluids through the respective first and second openings of the catheter member.

BRIEF DESCRIPTION OF THE DRAWINGS

Preferred embodiments of the present disclosure will be better understood with reference to the accompanying drawings wherein:

FIGS. 5-6 are side plan views of the leading end of the hemodialysis catheter;

FIG. 7 is a cross-sectional view taken along the lines 8-8 of FIG. 5;

FIG. 8 is a cross-sectional view taken along the lines 9-9 of FIG. 5;

FIG. 9 is a perspective view with parts separated of the leading end of the hemodialysis catheter;

DETAILED DESCRIPTION OF THE PREFERRED EMBODIMENTS

The exemplary embodiments of the catheter and methods of use disclosed are discussed in terms of medical catheters for the administration of fluids relative to the body of a subject and, more particularly, in terms of an acute hemodialysis catheter. However, it is envisioned that the present disclosure may be employed with a range of catheter applications including surgical, diagnostic and related treatments of diseases, body ailments, of a subject. It is further envisioned that the principles relating to the catheter disclosed include employment with various catheter related procedures, such as, for example, hemodialysis, cardiac, abdominal, urinary, intestinal, in chronic and/or acute applications. Moreover, the catheter can be used for administration or withdrawal of fluids such as, for example, medication, saline, bodily fluids, blood and urine.

In the discussion that follows, the term "proximal" or "trailing" will refer to the portion of a structure that is closer to a clinician, while the term "distal" or "leading" will refer to the portion that is further from the clinician. As used herein, the term "subject" refers to a human patient or other animal. The term "clinician" refers to a doctor, nurse or other care provider and may include support personnel.

Figure 1:
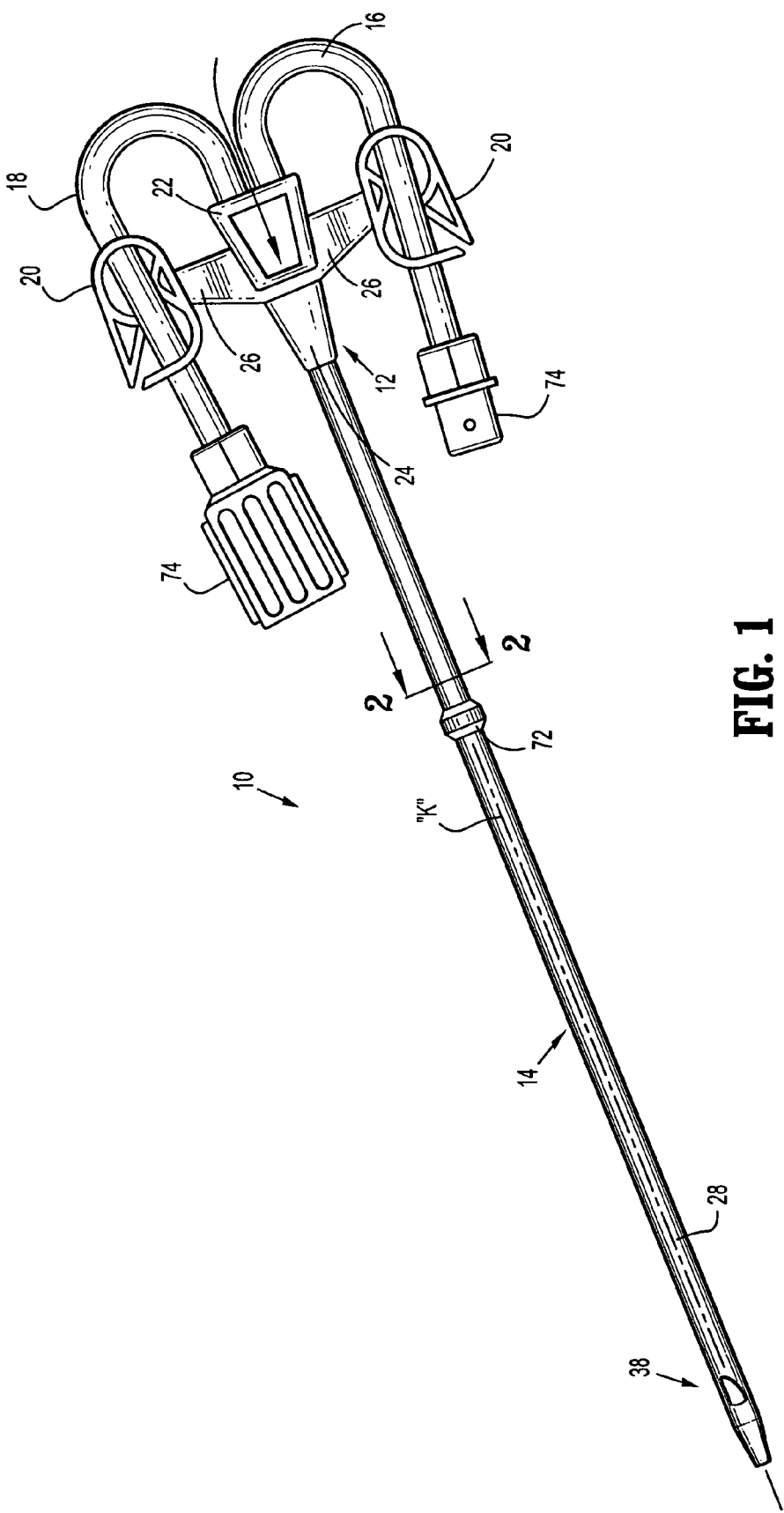
FIG. 1 is a perspective view of the acute hemodialysis catheter in accordance with the principles of the present disclosure.

Referring now to the drawings wherein like components are designated by like reference numerals throughout the several views, FIG. 1 illustrates in perspective view, the hemodialysis catheter 10 in accordance with the principles of the present disclosure. Catheter 10 includes several components assembled together, namely, catheter hub or housing 12, elongated catheter member 14 extending distally from the catheter hub 12 and first and second extension tubes 16, 18 extending proximally from the catheter hub 12. Catheter system 10 further includes a pair of clamps 20 which are attached about each of extension tubes 16, 18.

With continued reference to FIG. 1, catheter hub 12 is advantageously dimensioned for engagement by the clinician. Catheter hub 12 includes proximal or trailing housing section 22 adjacent extension tubes 16, 18 and distal or leading housing section 24 adjacent catheter member 14. Proximal housing section 22 is adapted to receive respective first and second extension tubes 16, 18 in secured relation therewith. In one preferred embodiment, extension tubes 16, 18 are secured within respective extension conduits (not shown) of catheter hub 12 via an interference or frictional fit, cements or adhesives. Distal or leading housing section 24 of catheter hub 12 defines central opening (not shown) which receives catheter member 14. Catheter member 14 may be secured within central opening of distal housing section 24 via an interference or frictional fit, and, possibly supplemented with cements or adhesives.

Catheter hub 12 may further include a pair of opposed wings 26 depending outwardly from the catheter hub 12. Wings 26 may serve as support elements to support first and second extension tubes 16, 18. In addition, it is contemplated that sutures may be wrapped about wings 26 to secure catheter hub 12 relative to the subject. In the alternative, wings 26 or catheter hub 12 may have an annular groove in its outer wall to receive the sutures. A suture may be wrapped within annular groove and subsequently secured relative to the subject.

Figure 2:
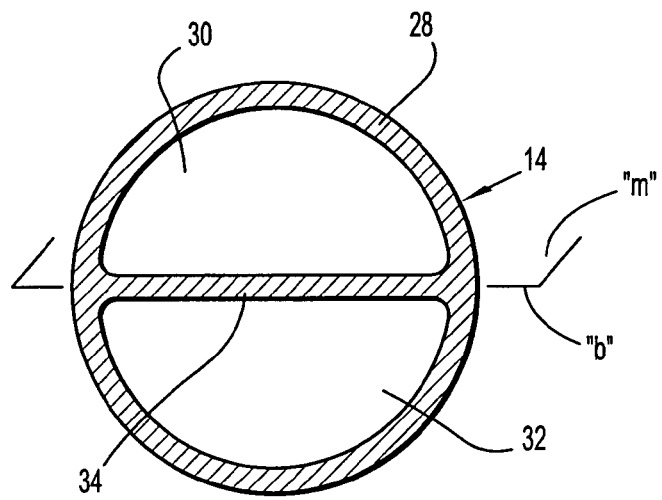
FIG. 2 is a cross-sectional view taken along the lines 2-2 of FIG. 1 illustrating a dual lumen catheter.
Figure 2A:
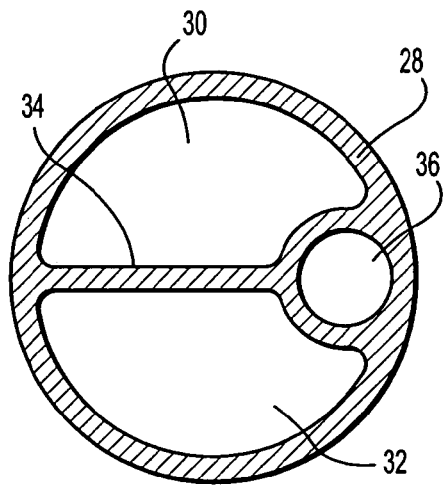
FIG. 2A is a view similar to the view of FIG. 2 illustrating an alternate embodiment incorporating a dual lumen catheter with a guide wire lumen.
Figure 2B:
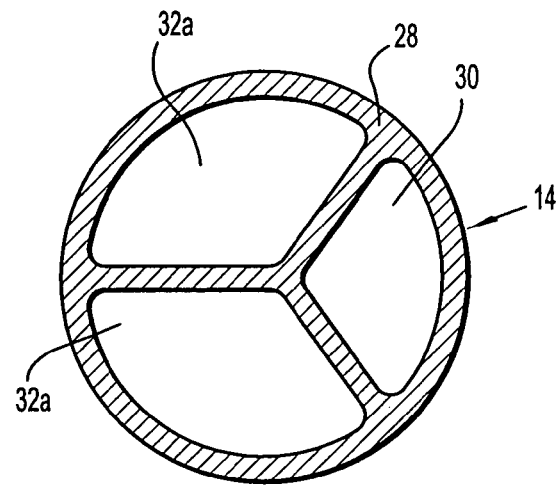
FIG. 2B is a view similar to the view of FIG. 2 illustrating an alternate embodiment incorporating a triple lumen catheter.

Referring now to FIG. 2, in conjunction with FIG. 1, elongated catheter member 14 will be discussed. Catheter member 14 defines longitudinal axis "k" and transverse axis "b" in transverse relation to the longitudinal axis "k". Catheter member 14 is preferably a dual lumen catheter having outer wall 28 and first and second longitudinal lumens 30, 32 separated by a septum wall 34 which may or may not extend the length the catheter member 14. Each of the first and second longitudinal lumens 30, 32 may define an oblong, kidney-shaped, or D-shaped opening in cross-section. Other lumen arrangements are also envisioned including circular, pie shaped etc. Coaxial lumens are also envisioned. As depicted in FIG. 2A, catheter member 14 may also include guidewire lumen 36 for reception and passage of a guidewire utilized to facilitate entry of the catheter member 14 within the vascular organ. Alternatively, one of first and second longitudinal lumens 30, 32 also may serve as the guidewire lumen in addition to its functioning to withdraw or deliver fluids. As a further embodiment, although hemodialysis catheter 10 is represented as a dual lumen catheter, single or triple lumen catheters are also envisioned. FIG. 2B illustrates a triple lumen catheter with longitudinal lumens 30, 32a, 32b.

Figure 3:
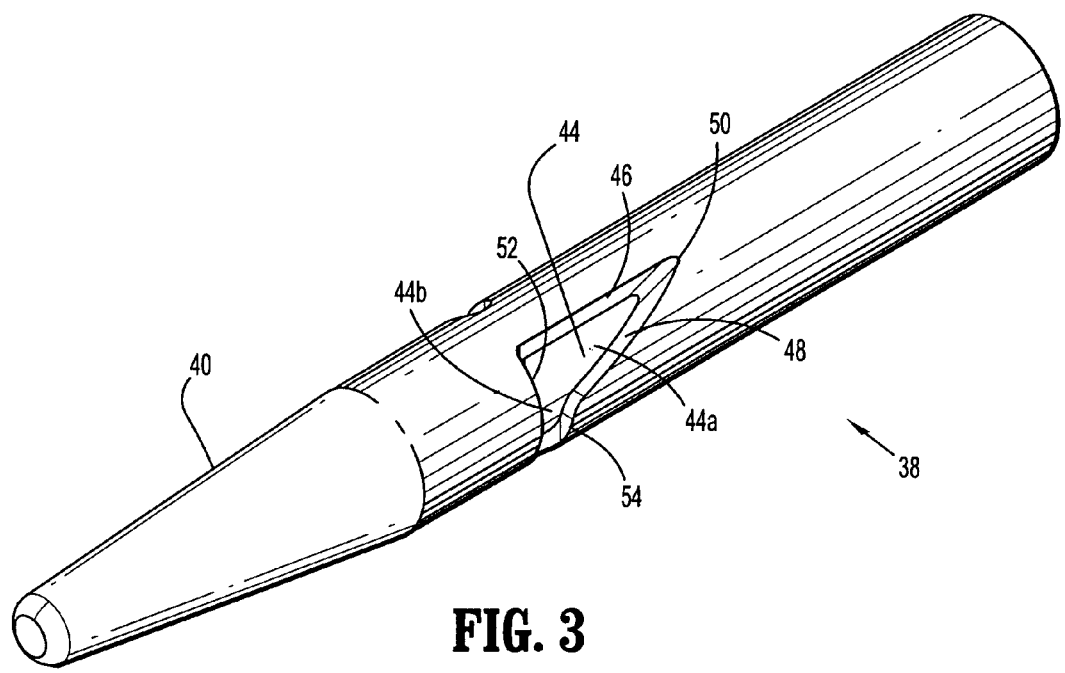
FIGS. 3-4 are perspective views of the leading end of the hemodialysis catheter.
Figure 4:
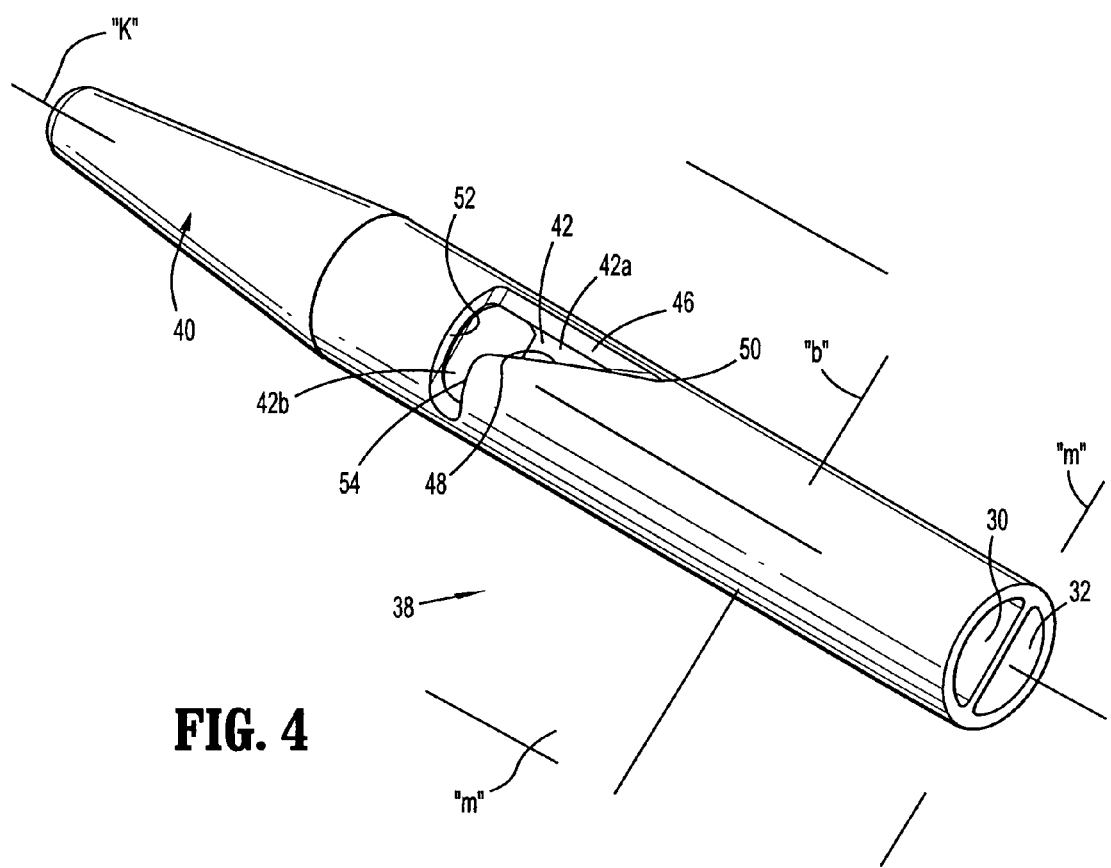

With particular reference to FIGS. 3-4, leading or distal end 38 of catheter member 14 will be discussed. Leading end 38 of catheter member 14 has catheter tip member 40 mounted thereto. Catheter tip member 40 will be discussed in greater detail hereinbelow. Leading or distal end 38 of catheter member 14 includes a pair of opposed openings 42, 44 arranged in its outer wall in diametrical relation and in fluid communication with respective first and second longitudinal lumens 30, 32. Each opening 42, 44 is spaced from catheter tip member 40. Each opening 42, 44 is characterized by having an arcuate recessed wall surface to define a partial generally arcuate opening as shown. Openings 42, 44 are symmetrically arranged about the longitudinal bisecting plane "m" of catheter member 14 (FIG. 4). Transverse axis "b" of catheter member 14 is coincident with bisecting plane "m". Openings 42, 44 permit passage of fluids during the procedure.

As best depicted in FIGS. 3-7, openings 42, 44 include proximal or trailing opening segments 42a, 44a and distal or leading opening segments 42b, 44b. Trailing opening segments 42a, 44a each define an internal transverse dimension relative to transverse axis "b" which increases from proximal to distal end to define an enlarged tear-drop shaped configuration as shown. Specifically, the wall portions defining opening segments 42a, 44a include first and second side surfaces 46, 48 which extend distally from a proximal locale or point of intersection 50. In one embodiment, first side surface 46 is in general parallel relation with the longitudinal axis "k". Second side surface 48 has an arcuate character and diverges outwardly from the longitudinal axis "k" and relative to first surface 46. First and second side surfaces 46,48 of trailing opening segments 42a, 44a may be linear or arcuate to provide a smooth inlet or outlet for the blood without substantially interrupting the flow of blood.

Distal or leading opening segments 42b, 44b are in communication with trailing opening segments 42a, 44a. In one embodiment, first side surface 46 extends continuously to end surface 52 which traverses longitudinal axis "k", e.g., is perpendicular to the longitudinal axis "k". Second side surface 48 may extend contiguously to an intermediate end surface 54 which traverses the longitudinal axis "k", preferably, in parallel relation with end surface 52. This configuration, in effect, may define a leading opening segment 42b, 44b having a polygonal or rectangular profile and extending in transverse direction to longitudinal axis "k" of catheter member 14. Leading segment 42b, 44b may accommodate greater fluid flow in the event a greater flow capacity is needed and may be incorporated into either or both openings 42, 44.

Figure 10:
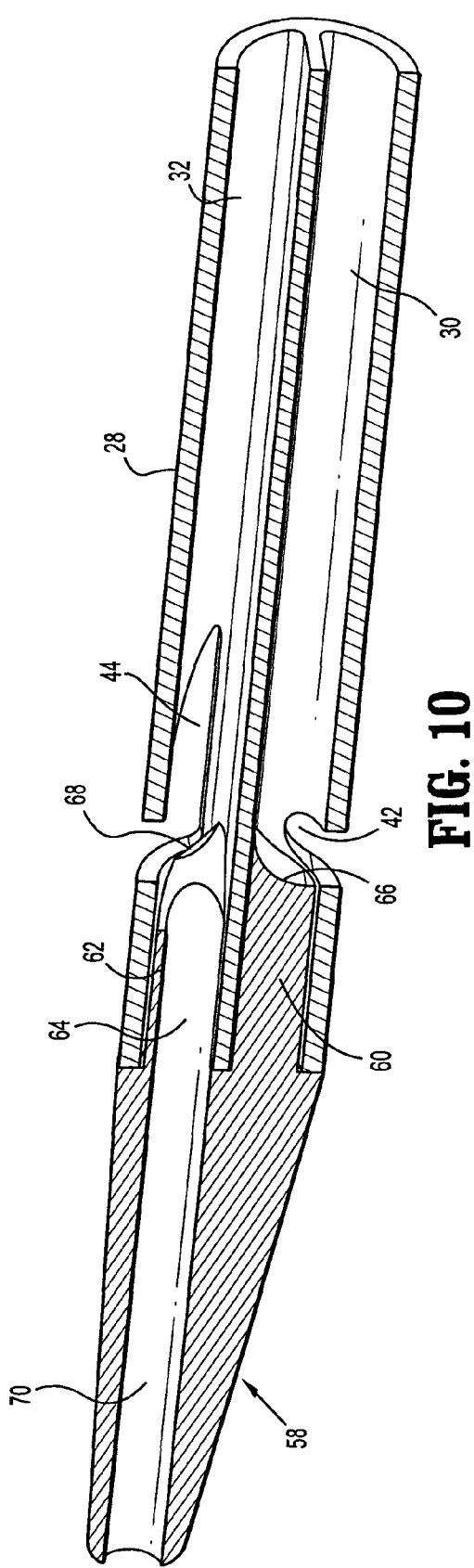
FIG. 10 is a side cross-sectional view taken along the lines $10^{-10}$ of FIG. 8.

Referring now to FIGS. 6-11, catheter tip member 40 will be discussed. Catheter tip member 40 includes proximal or trailing mounting member 56 and distal tapered portion 58 as best depicted in FIG. 9. Mounting member 56 cooperates with leading end 38 of catheter member to secure catheter tip member 40 to catheter member 14. In one embodiment, proximal mounting member 56 includes first and second extensions 60, 62 which are positionable within respective longitudinal lumens 30, 32 of catheter member 14, and are adapted to establish an interference relationship with the inner walls defining the first and second longitudinal lumens 30, 32. Adhesives may be utilized to further secure catheter tip member 40 to catheter member 14. Second extension 62 further defines guidewire lumen 64 which serves as an extension of longitudinal lumen 32 for passage of the guidewire as best shown in FIG. 10. Preferably, guidewire lumen 64 defines an inner diameter which substantially approximates the diameter of the guidewire intended for use with catheter 10 and less than an internal dimension of longitudinal lumen 32 to substantially minimize passage of fluid through the guidewire lumen 64. First extension 60 is devoid of a lumen. As best depicted in FIG. 10, proximal surfaces 66,68 of respective first and second extensions 60,62 are contoured and angulated with respect to longitudinal axis "k" to assist in directing flow of fluid to and from catheter member 14.

Figure 11:
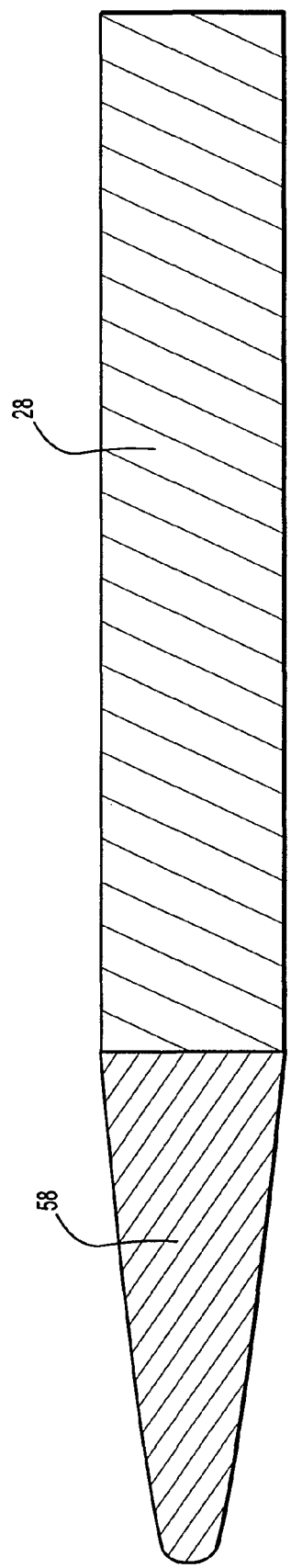
FIG. 11 is a side cross-sectional view taken along the lines 11-11 of FIG. 8.

Distal tapered portion 58 of catheter tip member 40 is preferably tapered along its length to define a narrow profile for initial insertion within the body tissue. Tapered portion 58 defines guidewire lumen 70 in communication with guidewire lumen 64 of second extension 62. Preferably, guidewire lumens 64,70 are a single lumen extending through catheter tip member 40 as shown. When viewed along one profile, catheter tip member 40 defines a linear taper throughout its length to define a right conical configuration as depicted in FIG. 11. However, when viewed along a second profile rotated 90 degrees as depicted in FIG. 10, distal tapered portion 58 of catheter tip member 40 defines an oblique conical configuration. With this arrangement, guide wire lumens 64, 70 may be in general longitudinal alignment with second longitudinal lumen 32 of catheter member 14. This facilitates passage of catheter member 14 along a guidewire.

Catheter tip member 40 may be fabricated from an elastomeric material or the like which presents an atraumatic surface to tissue. Any suitable biocompatible elastomer may be incorporated within catheter tip member 40. In an alternative embodiment, catheter tip member 40 is integrally or monolithically formed with leading end 38 of catheter member 14.

Catheter member 14 is preferably flexible and may be formed by conventional injection molding or extrusion means. Outer wall 28 of catheter member 14 may include reinforcing material if desired. Catheter member 14 may have a pre-curved configuration in its normal state, i.e., having a preformed bend which it normally assumes in the absence of an external stressor, to conform to a body cavity or vessel in which the catheter member is to be positioned. Alternatively, catheter member 14 may be devoid of any normally curved orientation.

Referring again to FIG. 1, catheter member 14 may further include at least one cuff 72 on its outer surface. Cuff 72 may include a fabric material and functions to be a site for tissue ingrowth for long term securing of catheter 10 in an indwelling position. For example, cuff 72 may reside in the tunnel formed during the tunneling procedure. More than one cuff 72 may also be provided. Catheter member 14 may also include radiopaque markings or strips to facilitate the location of catheter within the body with a fluoroscope.

First and second extension tubes 16, 18 may be any suitable tubing adapted to supply or withdrawal fluid to or from a body vessel. First and second extension tubes 16, 18 preferably include a compressible material whereby the tubes 16, 18 may be selectively compressed via clamps 20 to substantially close the opening within the tubes 16, 18. The free or trailing ends of extension tubes 16, 18 remote from catheter hub 12 have adapters 74 mounted thereto. Adapters 74 may be any conventional luer connector or adapter utilized in an environment for administrating fluids. One suitable connection is a luer connector which may incorporate an external thread or cam for securing to a fluid source. Adapters 74 may be secured to extension tubes 16, 18 by any of the aforementioned means including friction or tolerance fit, adhesives, cements, etc.

Clamps 20 are mounted about first and second extension tubes 16, 18. Each clamp 20 is adapted to move from a first open position in non compressive engagement with the respective extension tube 16, 18 to a second substantially closed position to compress the respective extension tube and close the lumen within the tube thereby preventing fluid flow in either direction.

The components of catheter 10 are fabricated from materials suitable for medical applications, such as, for example, polymerics or metals, such as titanium and stainless steel, depending on the particular catheter application and/or preference of a practitioner. Semi-rigid and rigid polymerics are contemplated for fabrication, as well as resilient materials, such as molded medical grade polyurethane, silicone, etc. Any sealing components of catheter 10 may be fabricated from low friction property materials such as polytetrafluoroethylene (PTFE) coated, PTFE impregnated, internally lubricated elastomers, etc. One skilled in the art, however, will realize that other materials and fabrication methods suitable for assembly and manufacture, in accordance with the present disclosure, also would be appropriate.

In a hemodialysis application, one adapter 74 may be connected to the hemodialysis machine to withdraw blood through, e.g., longitudinal lumen 30 and extension tube 16. The remaining adapter 74 is intended to return the blood through extension tube 18 and longitudinal lumen 32 for delivery to the patient. Clamps 20 may be manipulated between their respective first open and second closed positions as desired.

In use, either longitudinal lumen 30, 32 may serve as the intake lumen or the return lumen. For example, if lumen 30 is to serve as the intake lumen, the blood being received within opening 42 would tend to flow under suction supplied by the hemodialysis machine toward or within the narrower proximal segment 42a of the opening 42. However, the arcuate configuration of the opening 42 adequately accommodates this flow requirement. The blood being returned from the hemodialysis machine via return lumen 32 would flow under pressure through opening 44 adjacent the enlarged distal area or segment 44b of the opening 42. The enlarged distal area or segment 44b is dimensioned to permit sufficient blood flow without degrading flow performance. In addition, in that the blood is primarily being returned within the distal area or segment 44b of opening 44 downstream of the proximal segment 42a of corresponding opening 42, recirculation of "cleaned" blood is substantially minimized.

If catheter occlusion or thrombus formation is suspected, the clinician may reverse the flow of fluids through the line whereby longitudinal lumen 30 serves as the return lumen where blood is returned to the patient from the hemodialysis machine and longitudinal lumen 32 serves as the intake lumen. It is noted that symmetrical characteristics of openings 42, 44 enables either longitudinal lumen 30, 32 to function in the intake or return capacity.

Figure 12:
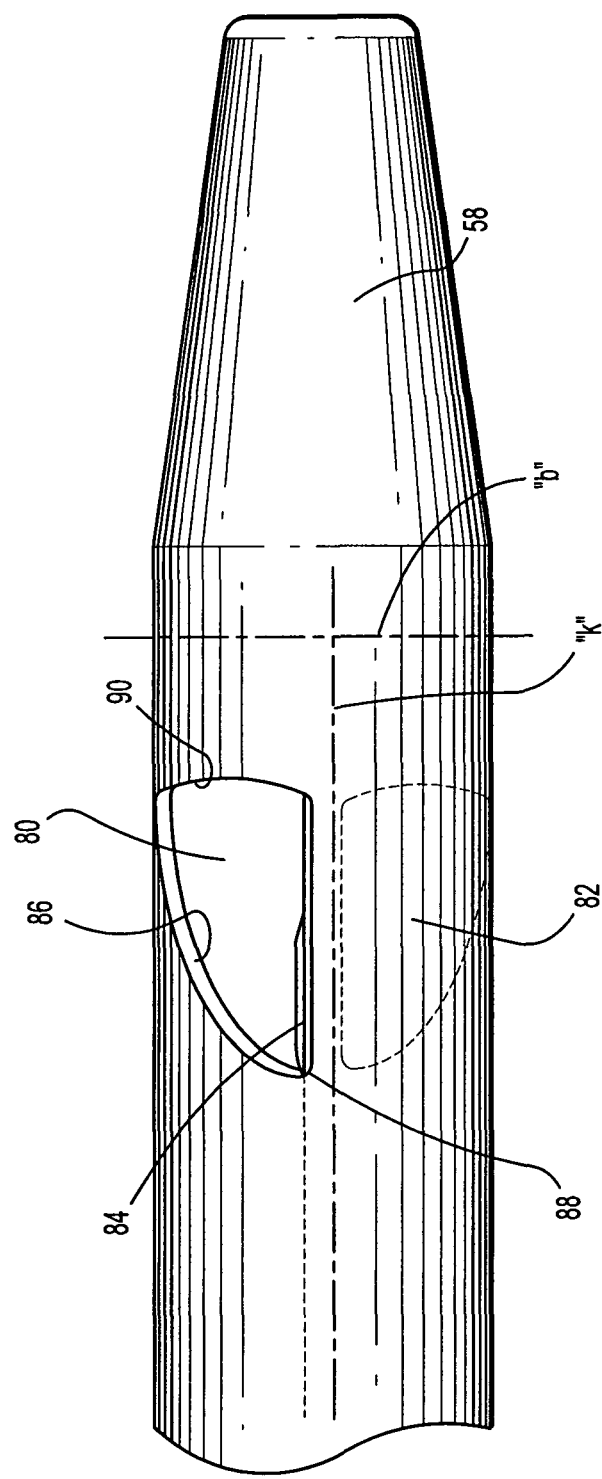
FIG. 12 is a side plan view of an alternate embodiment of the leading end of the hemodialysis catheter.

FIG. 12 illustrates an alternate embodiment of the present disclosure. In accordance with this embodiment, catheter member 14 includes first and second openings 80, 82 in communication with respective longitudinal lumens 30, 32 of catheter member 14. Opening 82 is shown in phantom. First and second openings 80, 82 are preferably symmetrically arranged about a median plane "m" bisecting the catheter member 14 and coincident with longitudinal axis "k" in a similar manner to the embodiment of FIG. 1. Openings 80, 82 each define first and second side wall surfaces 84, 86 which commence at proximal location 88 and extend along the longitudinal axis "k". Side wall surface 84 may be parallel to longitudinal axis "k" and side wall surface 86 diverges outwardly from the longitudinal axis "k" in the distal direction. Both side wall surfaces 84, 86 extend to end surface 90 which traverses longitudinal axis "k" of catheter member 14, i.e., and may generally extend along the transverse axis "b" in transverse relation to the longitudinal axis "k". Side and end wall surfaces 84, 86, 90 may have an arcuate contour to provide a smooth inlet or outlet for the blood without substantially interrupting the flow of blood through the openings. The catheter of the embodiment of FIG. 12 may be used in a similar manner to the embodiment of FIG. 1 and in a reverse flow capacity as discussed hereinabove. Specifically, the arrangement of openings 80, 82 define a distal opening segment which is greater than the proximal opening segment whereby blood may be withdrawn through the proximal segment of a first opening, e.g. opening 80, through longitudinal lumen 30 of catheter member 14 and returned via longitudinal lumen 32 and through the enlarged distal segment of opening 82.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A medical catheter, which comprises:
an elongate catheter member defining a longitudinal axis and a transverse axis transverse to the longitudinal axis, and having a proximal end and a distal end, the elongate catheter member including an outer member and at least one longitudinal lumen within the outer member for passage of fluids, the outer member defining an elongate opening there through in communication with the at least one longitudinal lumen and being spaced proximally from a distal end of the at least one longitudinal lumen and bound by wall portions of the outer member, the elongate opening permitting fluids to pass between the at least one longitudinal lumen and locations external to the elongate catheter member, and defining a transverse dimension increasing from proximal to distal;
the wall portions including a first side wall extending substantially parallel to the longitudinal axis, an end wall extending substantially parallel to the transverse axis and a second side wall which diverges outwardly from the first side wall, the end wall being positioned proximally of the distal end of the outer member, each of the elongate openings defining a transverse dimension increasing from a proximal end of the elongate opening to a distal end of the elongate opening.

2. The medical catheter according to claim 1 wherein the transverse dimension of the elongate opening is greatest adjacent the end wall.

3. The medical catheter according to claim 2 wherein the wall portion includes an intermediate wall coterminous with the second side wall and extending outwardly therefrom.

4. The medical catheter according to claim 3 wherein the intermediate wall is arranged in general parallel relation with the end wall.

5. The medical catheter according to claim 4 wherein the intermediate wall and the end wall generally extend along the transverse axis in general transverse relation with the longitudinal axis.

6. The medical catheter according to claim 1 wherein the elongate opening is a first elongate opening, the outer member further defines a second elongate opening, the at least one longitudinal lumen includes first and second longitudinal lumens, the first and second elongate openings within the outer member are in communication with the first and second longitudinal lumens, respectively, and are bound by respective wall portions of the outer member.

7. The medical catheter according to claim 6 wherein the elongate openings are arranged in symmetrical relation with respect to a median plane bisecting the elongate catheter member.

8. A medical catheter, which comprises:
an elongate catheter member defining a longitudinal axis, and having a proximal end and a distal end, the elongate catheter member including an outer member and at least one longitudinal lumen within the outer member, the outer member having an elongate opening there through in fluid communication with the at least one longitudinal lumen, the elongate opening being spaced proximally of a distal end of the at least one longitudinal lumen and being at least bound by inner wall surfaces of the outer member, the elongate opening defining an effective area along the longitudinal axis which increases from proximal to distal, the inner wall surfaces of the elongate opening including a first side wall surface extending substantially parallel to the longitudinal axis, an end wall surface extending transverse to the longitudinal axis, and a second side wall surface which diverges outwardly from the first side wall toward the distal end of the elongate catheter member, the end wall being spaced proximally of the distal end of the at least one longitudinal lumen, whereby when in a first mode of operation of the elongated catheter member, fluids are substantially withdrawn through a proximal area of the elongate opening and into the at least one longitudinal lumen, and when in a second mode of operation of the elongated catheter member, fluids are delivered from the at least one longitudinal lumen and substantially through a distal area of the elongate opening.

9. The medical catheter according to claim 8 wherein the first side wall surface and the second side wall surface generally converge at a proximal location.

10. The medical catheter according to claim 9 wherein the elongate opening defines a general tear drop shaped portion.

11. The medical catheter according to claim 9 wherein the elongate opening is a first elongate opening, the outer member further defines a second elongate opening, the at least one longitudinal lumen includes first and second longitudinal lumens, and the first and second elongate openings within the outer member are in communication with the first and second longitudinal lumens, respectively.

12. The medical catheter according to claim 11 wherein the first and second elongate openings are arranged in symmetrical relation with respect to a median plane bisecting the elongate catheter member.

13. The medical catheter according to claim 9 wherein the elongate opening is a first elongate opening, the outer member further defines second and third elongate openings, and the at least one longitudinal lumen includes first, second and third longitudinal lumens, and the first, second and third elongate openings within the outer member are in communication with the first, second and third longitudinal lumens, respectively.

14. A dialysis catheter, which comprises:
an elongate catheter member including an outer member defining proximal and distal ends and a longitudinal axis, and having first and second longitudinal lumens arranged in side by side relation within the outer member, the outer member including first and second elongate openings defined within wall surfaces of the outer member and arranged in symmetrical relation with respect to a longitudinal bisecting plane bisecting the elongate catheter member, the first and second elongate openings in respective fluid communication with the first and second longitudinal lumens and each defining an area within the wall surfaces greater at a distal location of the elongate opening relative to a proximal location of the elongate opening, each of the elongate openings being spaced proximally of a distal end of the respective first and second longitudinal lumens and bound by a first side wall surface extending substantially parallel to the longitudinal axis, an end wall surface extending transverse to the longitudinal axis, and a second side wall surface which diverges outwardly from the first side wall toward the distal end of the outer member, the first and second longitudinal lumens each being selectively adapted for removal of fluids where the fluids are substantially withdrawn through the area adjacent the proximal location of the elongate opening and for delivery of fluids where the fluids are delivered through the area adjacent the distal location of the elongate opening.

15. The dialysis catheter according to claim 14 including a catheter tip member mounted to the catheter member, the catheter tip member defining a tapered configuration.

16. The dialysis catheter according to claim 15 wherein the catheter tip member includes a guide wire lumen there through.

17. The dialysis catheter according to claim 16 wherein the catheter tip member includes first and second mounting extensions receivable within the respective first and second longitudinal lumens of the catheter member to connect the catheter tip member to the catheter member, the mounting extensions including internal contoured wall surfaces which cooperate to direct and receive fluids through the respective first and second openings of the catheter member.

18. The medical catheter according to claim 1, wherein the at least one longitudinal lumen extends to the distal end of the outer member.

19. The medical catheter according to claim 8, wherein the at least one longitudinal lumen extends to the distal end of the outer member.

20. The dialysis catheter according to claim 14, wherein the first and second longitudinal lumens each extend to the distal end of the outer member.

* * * * *